(12) United States Patent
O'Hare et al.

(10) Patent No.: US 9,170,215 B2
(45) Date of Patent: Oct. 27, 2015

(54) APPARATUS AND METHOD OF IMAGING A HETEROGENEOUS OBJECT

(71) Applicant: Hexagon Metrology, Inc., North Kingstown, RI (US)

(72) Inventors: Jonathan O'Hare, Warwick, RI (US); Stephen Darrouzet, West Warwick, RI (US)

(73) Assignee: Hexagon Metrology, Inc., North Kingstown, RI (US)

( * ) Notice: Subject to any disclaimer, the term of this patent is extended or adjusted under 35 U.S.C. 154(b) by 259 days.

(21) Appl. No.: 13/660,235

(22) Filed: Oct. 25, 2012

(65) Prior Publication Data

US 2014/0119501 A1    May 1, 2014

(51) Int. Cl.
| | | |
|---|---|---|
| G01N 23/00 | (2006.01) | |
| G01N 23/02 | (2006.01) | |
| A61B 6/03 | (2006.01) | |
| G01N 23/04 | (2006.01) | |
| A61B 6/12 | (2006.01) | |
| A61B 6/00 | (2006.01) | |

(52) U.S. Cl.
CPC ............... *G01N 23/046* (2013.01); *A61B 6/032* (2013.01); *A61B 6/12* (2013.01); *A61B 6/488* (2013.01); *A61B 6/504* (2013.01); *G01N 2223/404* (2013.01); *G01N 2223/419* (2013.01); *G01N 2223/61* (2013.01)

(58) Field of Classification Search
CPC .................. G01N 2223/404; G01N 2223/419; G01N 23/046; G01N 2223/61; A61B 6/032
See application file for complete search history.

(56) References Cited

U.S. PATENT DOCUMENTS

| | | | |
|---|---|---|---|
| 3,497,691 A | 2/1970 | Chen | 250/83.3 |
| 3,843,884 A | 10/1974 | Evans | 250/272 |
| 4,057,728 A | 11/1977 | Peschmann et al. | 250/374 |
| 4,780,897 A | 10/1988 | McDaniel et al. | 378/62 |

(Continued)

FOREIGN PATENT DOCUMENTS

| | | | | |
|---|---|---|---|---|
| EP | 0206735 | 12/1986 | | G01G 9/00 |
| WO | WO 2007/143698 | 12/2007 | | A61F 2/02 |

OTHER PUBLICATIONS

Djukic et al., "Enhancement of Tow Visualisation in Carbon Composites," The University of New South Wales, CRC for Advanced Composite Structures Ltd., CompTest 2008, 28 pages.

(Continued)

*Primary Examiner* — Glen Kao
*Assistant Examiner* — Dani Fox
(74) *Attorney, Agent, or Firm* — Sunstein Kann Murphy & Timbers LLP (57) ABSTRACT

An imaging method positions a heterogeneous object within a fixture having a chamber. The fixture also has a valve for receiving a gas and normally sealing the chamber. Thus, the object is within the chamber. Next the method positions the fixture within an active region of a CT machine, fluidly connects a gas line to the valve, and injects an inert gas into the chamber through the gas line and the valve. The inert gas may include one or more of the xenon, argon, and krypton. The method then increases the pressure within the sealed chamber to increase the density of the gas within the chamber, and directs x-ray energy toward the active region of the CT machine to produce a plurality of two-dimensional images of the object and the pressurized gas. Finally, the method generates a three-dimensional representation of the object from the plurality of images.

18 Claims, 5 Drawing Sheets

(56) References Cited

U.S. PATENT DOCUMENTS

| | | | | |
|---|---|---|---|---|
| 5,271,401 | A | 12/1993 | Fishman | 128/654 |
| 5,444,255 | A | 8/1995 | Schmidt et al. | 250/385.1 |
| 5,855,682 | A | 1/1999 | Yoneda | 118/723 VE |
| 6,146,657 | A | 11/2000 | Unger et al. | 424/450 |
| 6,241,966 | B1 | 6/2001 | Albert et al. | 424/9.3 |
| 7,062,012 | B1 * | 6/2006 | Chng et al. | 378/57 |
| 2010/0256748 | A1 | 10/2010 | Taylor et al. | 623/1.46 |

OTHER PUBLICATIONS

Hendee et al., "Chapter 15 Computed Tomography," Medical Imaging Physics, Fourth Edition, 2002, pp. 251-263.

Ionescu et al., "Spatial Resolution Limits of Multislice Computed Tomography (MS-CT), C-arm-CT, and Flat Panel-CT (FP-CT) Compared to MicroCT for Visualization of a Small Metallic Stent," Academic Radiology, vol. 18, No. 7, Jul. 2011, pp. 866-875.

Lam et al., "Micro-CT imaging of rat lung ventilation using continuous image acquisition during xenon gas contrast enhancement," J Appl Pysiol, vol. 103, Aug. 9, 2007, pp. 1848-1856.

Chen et al., "A novel drug-eluting stent spray-coated with multilayers of collagen and sirolimus," *Journal of Controlled Release*, vol. 108, May 30, 2005, pp. 178-189.

Connolley et al. "X-ray micro-tomography of a coronary stent deployed in a model artery," *Medical Engineering & Physics*, vol. 29, Mar. 6, 2007, pp. 1132-1141.

International Searching Authority, International Application No. PCT/US2013/063702 dated Dec. 6, 2013, together with the Written Opinion of the International Searching Authority, 14 pages.

* cited by examiner

APPARATUS AND METHOD OF IMAGING A HETEROGENEOUS OBJECT

FIELD OF THE INVENTION

The invention generally relates to generating images of objects and, more particularly, the invention relates to generating detailed images of heterogeneous objects.

BACKGROUND OF THE INVENTION

Coordinate measuring machines (CMMs) are the gold standard for accurately measuring a wide variety of work pieces. For example, CMMs can measure critical dimensions of aircraft engine components, surgical tools, and gun barrels. Precise and accurate measurements help ensure that their underlying systems, such as an aircraft in the case of aircraft components, operate as specified.

Recently, those in the art have begun using computed tomography (CT) systems as CMMs for coordinate metrology. As known by those in the art, a CT system generates three-dimensional images of an object as a function of the attenuation of its x-rays by the object. Some materials, such as metal, may attenuate x-rays sufficiently under typical x-ray power settings, to generate an appropriate image. Other materials, however (e.g., polymers), may not sufficiently attenuate x-rays at the same or similar power settings.

This creates problems for heterogeneous objects. More specifically, CT imaging techniques known to the inventors do not adequately image objects made from heterogeneous materials in a way that is non-invasive or non-destructive. For example, those techniques cannot adequately image a stent, which is made from a metal mesh frame supporting one or more polymers. Although the metal mesh should adequately attenuate the x-rays, the polymer typically does not. Accordingly, rather than producing an image of the entire stent, the noted techniques may produce an image of the metal mesh without the polymers. Indeed, such an image does not have enough information to measure many of its important features, such as those features formed from polymers.

SUMMARY OF VARIOUS EMBODIMENTS

In accordance with one embodiment of the invention, a method of imaging a heterogeneous object positions the heterogeneous object within a fixture having a chamber. The heterogeneous object has a first portion and a second portion, where the first portion has the property of attenuating x-rays more than the second portion. After the object is in the chamber, the method adds an inert gas to the chamber, seals the chamber to substantially contain the gas within the chamber, and increases the pressure within the sealed chamber as a function of the density of the second portion of the object. The gas may include one or more of the xenon, argon, and krypton. The density of the gas increases with the increased pressure within the sealed chamber, thus producing the contrast. The method also penetrates the object with x-rays to produce a plurality of images of the object. The pressurized gas contrasts with the second portion of the object in at least some of the plurality of images. After directing x-rays toward the object, the method generates a three-dimensional representation of the object using (at least) the contrast produced by the pressurized gas in the plurality of images.

Among others, the gas may be a noble gas, such as xenon. As such, the gas should not cause a destructive reaction with the object. The x-rays may be directed from a CT machine generating the x-rays. To obtain a three-dimensional view of the object, the method also may rotate the chamber to produce the plurality of images.

The pressure may range from any of a number of pressures, such as from about 1 atmosphere to about 50 atmospheres. Moreover, when changing the pressure within the sealed chamber, the method may generate at least one test image of the object at a first pressure, and then change the pressure within the chamber as a function of the contrast between the second portion and the gas as shown in the test image. In illustrative embodiments, the three-dimensional representation of the object may show topological object details, thus enabling measurement of at least one of the topological object details.

In accordance with another embodiment of the invention, a method of imaging a heterogeneous object positions a heterogeneous object within a fixture having a chamber. The fixture also has a valve for receiving a gas and normally sealing the chamber. Thus, the object is within the chamber. Next the method positions the fixture within an active region of a CT machine, fluidly connects a gas line to the valve, and injects an inert gas into the chamber through the gas line and the valve. The inert gas may include one or more of the xenon, argon, and krypton. The method then increases the pressure within the sealed chamber to increase the density of the gas within the chamber, and directs x-ray energy toward the active region of the CT machine to produce a plurality of two-dimensional images of the object and the pressurized gas. Finally, the method generates a three-dimensional representation of the object from the plurality of images.

In accordance with other embodiments of the invention, a system for imaging a heterogeneous object has a fixture with 1) a chamber for receiving an object, and 2) a valve for receiving a gas and normally sealing the chamber. The system also has a CT machine with an active region sized to receive the fixture, a mechanism for adding inert gas into the chamber through the valve, and a mechanism for increasing the pressure within the sealed chamber to increase the density of the gas within the chamber. In addition, the system further has a mechanism for directing x-ray energy toward the active region of the CT machine to produce a plurality of images of the object and the pressurized gas. The plurality of images show the pressurized gas and object as having contrasting shades. Finally, the system has a mechanism for generating a three-dimensional representation/image of the object from the plurality of images.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

In illustrative embodiments, an x-ray imaging system captures low density/attenuation portions of a heterogeneous object that normally are invisible to x-rays. In fact, the system can capture that image without damaging or substantially altering any portion of that object. To that end, the system seals the heterogeneous object within the gas filled chamber of a fixture. The pressure within the chamber is set, and the gas is selected, to provide sufficient image contrast between the low attenuation portions of the object and the pressurized gas. The pressurized gas forms a boundary with the low attenuation portions of the object, consequently causing it (the gas) to have a boundary topology that is substantially identical to the portion of the object it bounds.

Using this technique, the x-ray system captures a plurality of two-dimensional images of the pressurized gas and the object, visually detailing the topology, size, and shape of the low attenuation portions of the object. Of course, the x-ray system also captures the high attenuation portions of the object in those same images. These two-dimensional images subsequently can be converted into a dimensionally and structurally accurate three-dimensional representation of the actual object. Accordingly, conventional metrology techniques may accurately measure the dimensions of the object without having to make contact with it. Details of illustrative embodiments are discussed below.

Figures 1, 2:
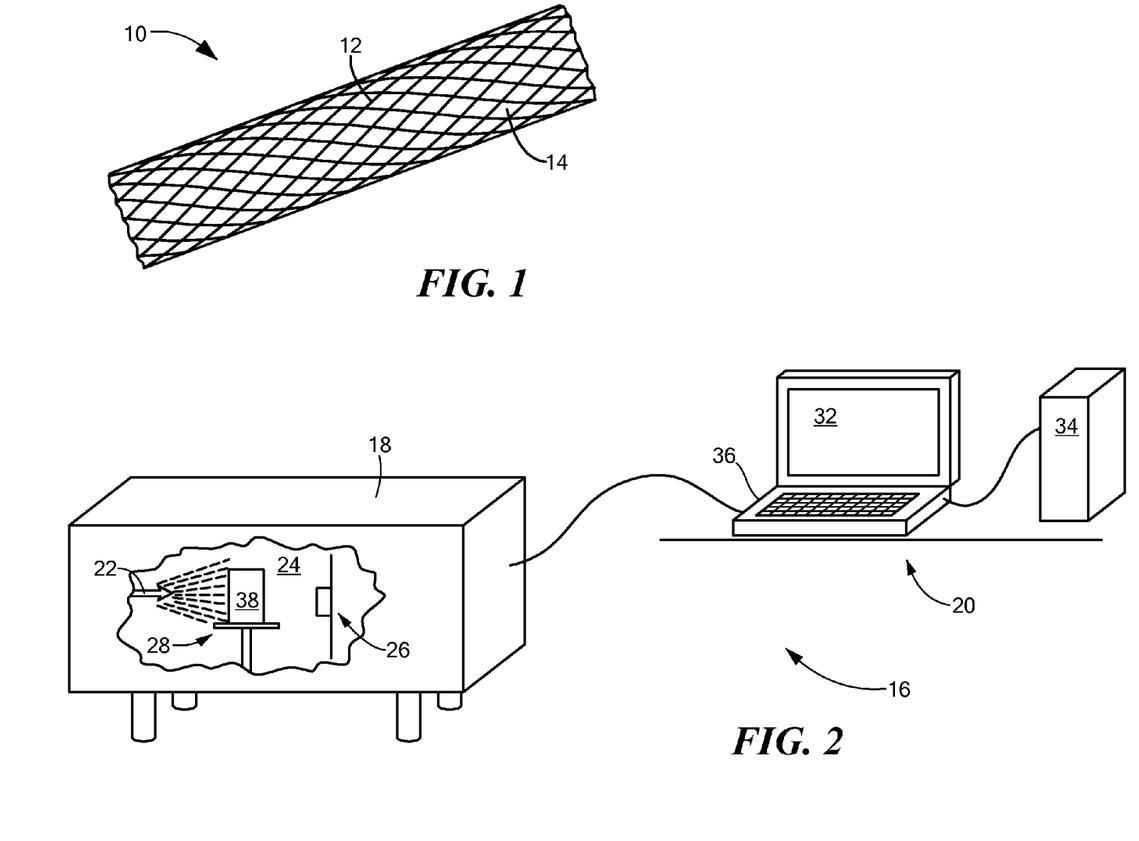
FIG. 1 schematically shows a heterogeneous object that may be imaged in accordance with illustrative embodiments of the invention.
FIG. 2 schematically shows a system for imaging a heterogeneous object, such as the heterogeneous object of FIG. 1, in accordance with illustrative embodiments of the invention.

FIG. 1 schematically shows a heterogeneous object 10 that may be imaged in accordance with illustrative embodiments of the invention. Specifically, the object 10 shown in FIG. 1 is a conventional stent, which is intended to be surgically implanted within a damaged artery. For example, a cardiologist may implant a stent into an artery of a patient after removing arterial plaque that caused a heart attack. Accordingly, the physical makeup and composition of the stent can be the difference between life and death. Stated another way, inaccurate dimensions or ill-defined structures can have catastrophic effects to the patient.

As known by those skilled in the art, a stent is a tubular device commonly having a flexible metal skeleton or mesh 12 that supports a fabric or polymeric substrate 14. Among other things, the substrate 14 may include medication or other substances intended to ensure that the patient's artery does not become blocked again. To check its dimensions, to the inventors' knowledge, those skilled in the art manually inspect the stents under a microscope. Such a process is time-consuming and inherently inaccurate.

Use of a current, state-of-the-art computed tomography system 16 ("CT systems 16, FIG. 2") also is not feasible because the polymeric or fabric portion of the stent is invisible to x-rays. In other words, the polymeric (or fabric) portion of the stent does not adequately attenuate x-rays to produce a complete image—it lacks sufficient contrast to the surrounding air. Accordingly, a conventional x-ray image of a stent undesirably shows the metal mesh 12 only. Such an image is not adequate for precisely measuring the dimensions of the stent. The inventors solved this problem by using x-ray imaging techniques for imaging a stent/object 10 that is engulfed or encapsulated by a high density inert gas under pressure. Such a technique nondestructively and accurately images fine details of the stent.

It should be noted that discussion of the stent is for illustrative purposes only. Other heterogeneous objects 10 similarly benefit from the systems and methods described herein. For example, illustrative embodiments can apply to a wide variety of different devices, such as artificial heart valves, drug delivery devices, coated tubes, electronic devices, other medical devices, coatings on microelectronics, consumer packaging, insulated wires, and a wide variety of other objects 10. Accordingly, discussion of a stent or other heterogeneous object 10 is not intended to limit all embodiments of the invention.

FIG. 2 schematically shows a system 16 that can image a heterogeneous object 10 in accordance with illustrative embodiments of the invention. As shown, the system 16 includes a conventional computed tomography machine ("CT machine 18") coordinated and controlled by an accompanying computer system 20. The CT machine 18 is shown in a cut-away view the detail some of its interior components. Specifically, like other CT machines, the CT machine 18 in this figure has an x-ray source 22 that transmits x-rays (typically) in a generally cone-shaped pattern (a/k/a a "cone beam"), toward and through an object 10 within its interior region. This interior region, which contains the object 10 being imaged as it is receiving x-rays, is referred to herein as an "active region 24." As known by those skilled in the art, the object 10 attenuates the x-rays to some degree, changing the pattern of x-rays on the opposite side of the object 10. A detector 26 on the opposite side of the object 10 detects this pattern, producing a two-dimensional representation/image of the object 10.

To obtain a three-dimensional representation/image, however, the system 16 moves the position of the object 10 relative to the x-ray source 22 and detector 26. Some CT machines rotate the x-ray source 22 and detector 26 while leaving the object 10 stationary. Other CT machines, such as that shown in FIG. 2, rotate the object 10, but keep the x-ray source 22 and detector 26 stationary. Of course, various embodiments may use either type of arrangement. In the latter case, the object 10 may be positioned on a rotating device, such as the platter of a rotary table 28. Among other ways, the rotary table 28 may be configured to precisely rotate the object 10 a predefined amount each time it generates a two-dimensional image. For example, the CT machine 18 may take 1000 to 2000 two-dimensional images of the object 10 on the platter. These two-dimensional images, which are taken from slightly different perspectives, often are referred to in the art as "projections."

Conventional software techniques convert this plurality of two-dimensional images/projections into a detailed, comprehensive three-dimensional representation of the object 10. For example, the computer system 20, which has a display device 32, a CPU/memory/logic within a chassis 34 (i.e., a computer), input device 36, and other conventional components, may execute these conventional software routines to generate a three-dimensional representation of the object 10.

Rather than place it directly on the rotary table 28, illustrative embodiments position the object 10 to be scanned/imaged within a gas filled, sealed fixture 38 that is removable from the interior of the CT machine 18. The fixture 38, with the object 10 in its interior, thus is positioned on the rotary table 28.

Figure 3:
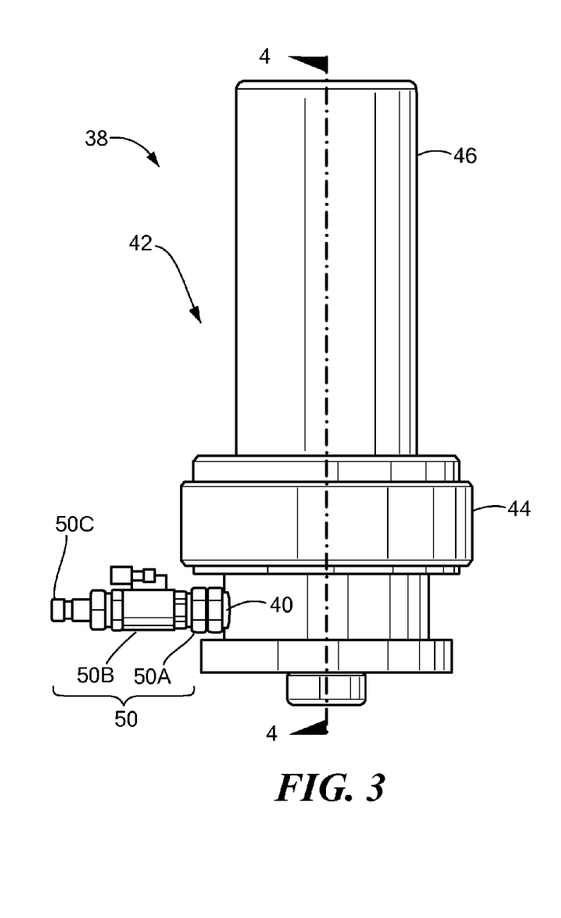
FIG. 3 schematically shows a side view of an imaging fixture for imaging a heterogeneous object in accordance with illustrative embodiments of the invention.

More specifically, FIG. 3 shows a perspective view of the fixture 38 configured in accordance with illustrative embodiments of the invention. As shown, the fixture 38 has an inlet 40 for receiving a gas, and a body 42 forming an interior chamber 43 (FIGS. 4-5, discussed below) for receiving and containing both the object 10 and a pressurized gas. Indeed, to facilitate imaging, the portion of the fixture 38 containing the object 10 should be formed primarily from a low density material that does not substantially attenuate x-rays. Among other things, the fixture 38 can have a cylindrical shape (or other shape) and be formed from a carbon fiber, or a polymeric or plastic material, such as polyvinyl chloride or nylon. As discussed below, another important quality of the fixture 38 is its capability of sealing specific pressurized gasses within its interior (discussed below) while remaining substantially transparent to x-rays. Those skilled in the art can select the appropriate materials to provide both functions.

Figure 4:
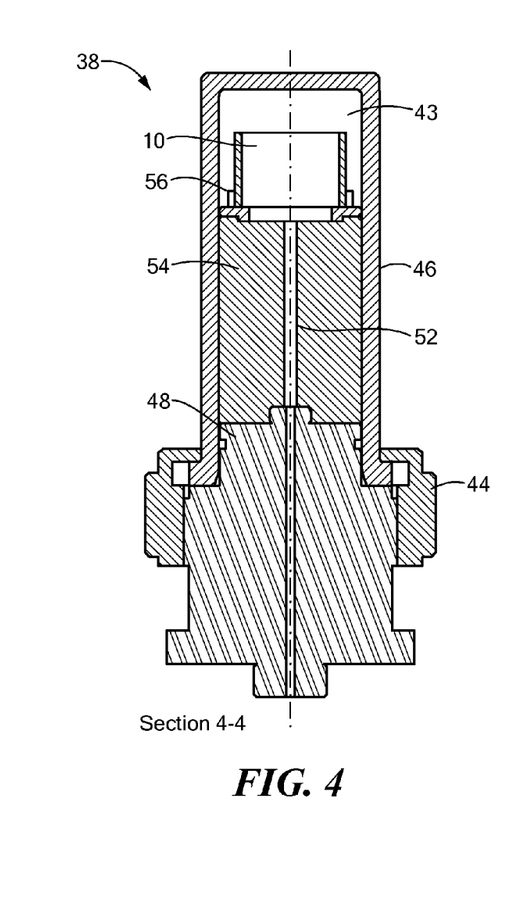
FIG. 4 schematically shows a cross-sectional view of the fixture of FIG. 3 along section line 4-4.
Figure 5:
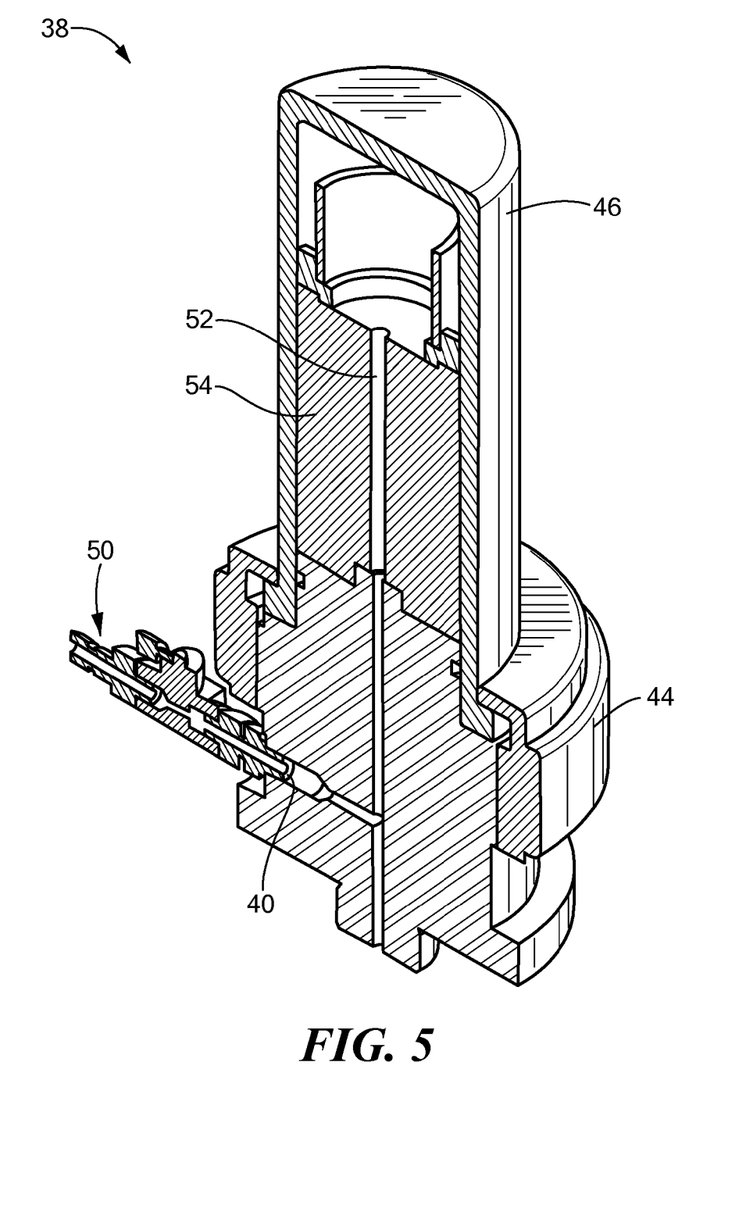
FIG. 5 schematically shows a cross-sectional, perspective view of the fixture of FIG. 3 across a section plane that is generally orthogonal to the section plane shown in FIG. 4.
Figure 6:
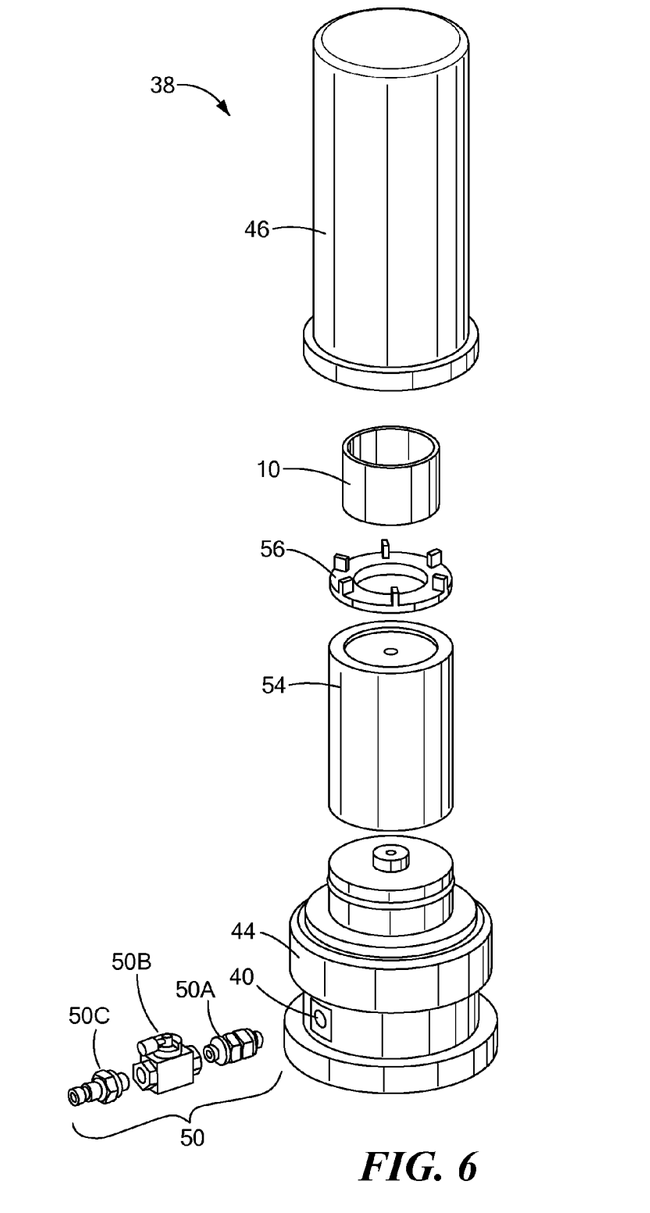
FIG. 6 schematically shows a perspective, exploded view of the fixture shown in FIG. 3.

FIGS. 4-6 schematically show more details of the fixture 38 in accordance with illustrative embodiments of the invention. Specifically, FIG. 4 schematically shows a cross-sectional view of the fixture 38 of FIG. 3 along section line 4-4, while FIG. 5 schematically shows a cross-sectional, perspective view of the fixture 38 of FIG. 3 across a section plane that is generally orthogonal to the section plane shown in FIG. 4. For further detail, FIG. 6 schematically shows a perspective, exploded view of the fixture 38 shown in FIG. 3.

As shown, the body 42 is made up generally of two interlocking housing components—namely, a base housing 44 having a port for receiving a gas, and a corresponding chamber housing 46 that locks onto the base housing 44 and forms a chamber 43 containing the gas and the object 10. Among other ways, the housings 44 and 46 may lock together either with a snap-fit connection, or a threaded connection using a double helix thread pattern.

The chamber housing 46 should have minimal x-ray attenuation qualities, while the base does not necessarily have such a requirement. In preferred embodiments, the chamber housing 46, or at least the top portion of the chamber 43, is substantially transparent to x-rays. The chamber housing 46 also preferably has a high-pressure relief valve (not shown) in case the pressure exceeds some prescribed upper limit (e.g., 35 atmospheres or 75 atmospheres). To make a sealed connection between the housings 44 and 46, the fixture 38 has an O-ring 48 between the top, outer dimension of the base housing 44 and the bottom, inner dimension of the chamber housing 46.

As best shown in FIG. 5, the housing has a valve mechanism 50 coupled with the housing inlet 40, and a gas channel 52 that directs the gas through the interior of the fixture 38 and into the chamber 43. The fixture 38 also includes a riser member ("riser 54") that forms at least a portion of that gas channel 52. The riser 54 also has another function—controlling the gas volume of the chamber 43 by displacement. Specifically, the volume of gas used can have a significant impact on the cost of the process. The inventors discovered that they could minimize the amount of gas used in the process by permitting the least amount of chamber volume for a given use.

To that end, the housings 44 and 46 and fixture 38 may be distributed and used as a kit with a plurality of different risers 54 for each fixture 38. Each riser 54 thus may have a different height and used depending on the size of the object 10 being imaged. For example, if the object 10 has a height of 5 inches, then the system 16 may incorporate a riser 54 that permits a clearance of 6 inches from the top of the chamber 43. Alternatively, as another example, if the object 10 has a height of 2 inches, then the system 16 may incorporate a riser 54 that permits a clearance of 2.5 inches or 3 inches from the top of the chamber 43. In illustrative embodiments, the riser 54 is formed from plastic or other similar low attenuation material. Other embodiments may use other materials.

It should be noted that the riser 54, or set of risers 54, are optional components. Instead, various embodiments simply may position the object 10 within the chamber 43 without the riser 54 at all. The size of the chamber 43 thus may be configured to image a specific item or set of items having a maximum height. In fact, the housings 44 and 46 can be distributed in various sizes (in height, width, and/or shape), either with or without the risers 54, to accommodate different types of devices/objects 10.

Some embodiments secure a positioning ring/member 56 on the top surface of the riser 54 to precisely position the object 10. Again, as with the housings 44 and 46, the positioning ring 56 should have a substantially low attenuation impact on x-rays.

As noted above, the inlet 40 to the gas channel 52 preferably has a valving mechanism that normally seals the interior of the chamber 43 when in the closed position. FIGS. 3, 5, and 6 show one type of valving mechanism that can accomplish the required functions. To that end, the value mechanism has an inlet fitting 50A for sealingly connecting with the gas inlet 40 of the base housing 44, a ball valve 50B coupled with the fitting to control gas flow, and an external quick connect/disconnect fitting 50C for connecting with a tube or hose from a gas source. Of course, those skilled in the art can use other valving mechanisms and thus, the valving mechanism described in the figures is for illustrative purposes only.

Figure 7:
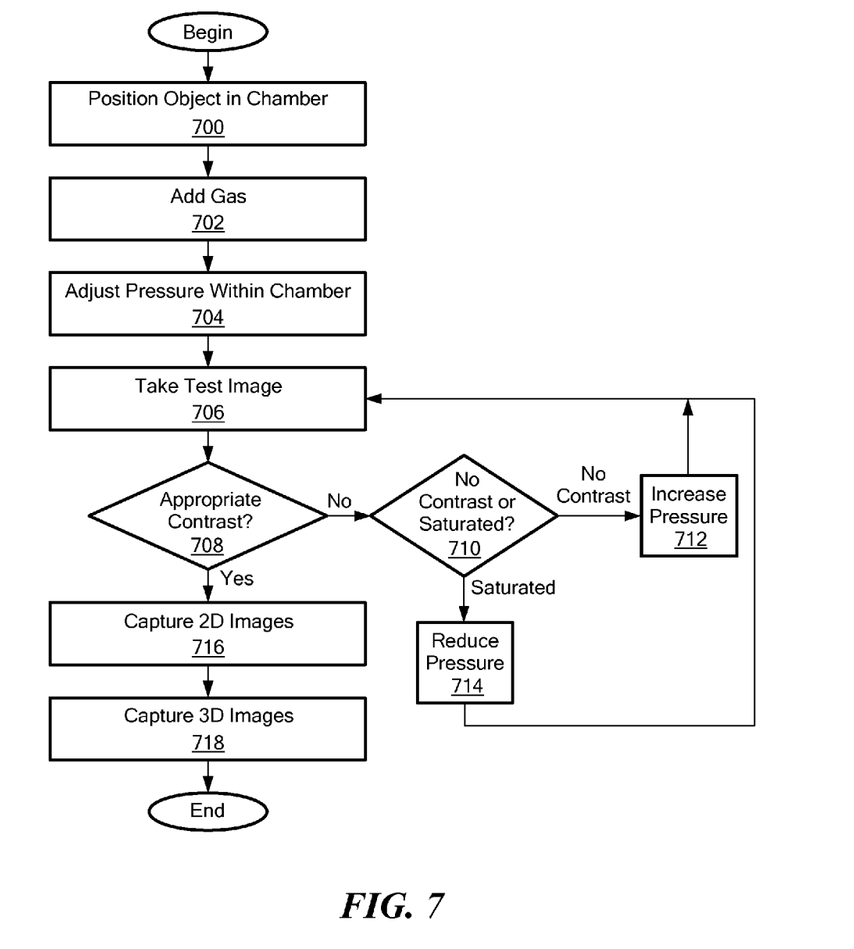
FIG. 7 shows a method of using the system of FIG. 2 to image a heterogeneous object in accordance with illustrative embodiments of the invention.

FIG. 7 shows a process of imaging a heterogeneous object 10 in accordance with illustrative embodiments of the invention. This process is a simplified version of what could be a much longer process. Accordingly, the process may entail additional steps that are not discussed in FIG. 7. Moreover, some embodiments may perform various steps in a different order than that described. Those skilled in the art should be able to make appropriate changes to the order and number of steps in the process, and still meet the spirit of various embodiments.

The process begins at step 700, which positions the object 10 in the chamber 43. To that end, an operator or technician manually separates the chamber housing 46 from the base housing 44, and places the object 10 (e.g., a stent) on the positioning ring 56. The operator then reconnects the chamber housing 46 to the base housing 44. As noted, the O-ring 48, which is squeezed between the base housing 44 and the chamber housing 46, ensures that the chamber 43 is substantially sealed for the intended gasses being used.

Next, at step 702, the process adds an appropriate gas through the valve mechanism 50 to the chamber 43. To that end, the technician can connect a hose from a gas source to the quick connect fitting 50C of the valve mechanism 50. The valve mechanism 50 then may be opened to permit a prescribed amount of gas into the interior chamber 43. Among other things, the amount of gas depends upon the materials making up the object 10, the size of the chamber 43, and the type of gas being used. After filling the chamber 43 to the appropriate level, the technician closes the valve mechanism 50 and removes the hose from the fitting.

Alternative embodiments may keep the gas line connected to the quick connect fitting 50C. For example, this may be the case when used with CT machines that rotate around the object 10 being imaged. As a second example, the base housing 44 of the fixture 38 may have an annular bearing or rotatable part that rotates freely relative to the chamber housing 46.

As noted above, the gas should have no substantial effect on the object 10. For example, the gas should not damage or oxidize the object 10. Moreover, to appropriately attenuate x-rays, the gas should have a relatively high density capable of attenuating x-rays, particularly when subjected to appropriate pressures. In illustrative embodiments, the gas is an inert gas, such as a noble gas. More specifically, the gas preferably is a pure gas or mixture having one or more of xenon, argon, and krypton. For example, the gas can include components of all three gases, along with other gases. As another example, the gas can be a substantially pure gas, such as substantially pure xenon. Some embodiments may use other gases, depending upon the application.

The process continues to step 704, which adjusts/increases the pressure within the chamber 43. This increased gas density ideally increases the gas density to a point where it sufficiently attenuates x-rays to provide meaningful contrast between it and the low attenuating material portion of the object 10. In preferred embodiments, the gas is dense enough to provide a contrasting boundary (with the low attenuating portion of the object 10) that is readily visible on the ultimately formed two-dimensional images/projections. As such, that boundary should have substantially accurate topological and structural details at least of the low attenuating portions of the object 10.

To those ends, the technician increases the pressure using conventional methods (e.g., connecting the valve mechanism 50 to a positive pressure source), which, as mentioned, correspondingly increases the density of the gas. The amount of the increase in pressure at this step can be based upon empirical data of prior use. Alternatively, the amount of increased pressure can be relatively arbitrary, and will be checked and adjusted in subsequent steps (steps 706-714) to ensure proper calibration.

The amount of pressure depends upon the gas being used. For example, increasing the pressure up to about 27-29 atmospheres should provide satisfactory attenuation when using xenon. Other gases, however, may require higher or lower pressures greater than about 1 atmosphere. Of course, the fixture 38 must be configured to withstand such high pressures.

At this point, the pressure may or may not be sufficient enough to provide adequate contrast for capturing details of the low attenuating portion of the object 10. If not, then the system 16 may be tuned to have appropriate contrasts. The process thus continues to step 706, which takes a "test image" of the object 10—to determine if the contrast is appropriate. The x-ray source 22 thus transmits penetrating x-rays toward the object 10. The voltage or intensity of the x-rays should be commensurate with the amount to appropriately image the higher attenuating portion of the object 10. For example, with a stent, the voltage should be sufficient to image the metal mesh 12. Of course, this higher energy prevents the polymer substrate 14 from attenuating enough of the x-rays to produce meaningful image data. The high density, pressurized gas solves this problem.

Step 708 thus determines if there is an appropriate amount of contrast between the pressurized gas and the low attenuation portion of the object 10. For example, when viewing the test image, the low attenuation portions of the object 10 may be substantially clear and have a defined, visually perceptible boundary between it and the darker gas.

To that end, after passing x-rays through the fixture 38 and object 10, the CT machine 18 transmits the raw data to the computer, which generates a two dimensional image of the object 10. The two-dimensional test image may be displayed on the display device 32 of the computer system 20, or printed out as a hard copy for review by the technician. Accordingly, the technician reviews the test image at step 708 to determine if there is enough contrast between the gas and the low attenuation portions of the object 10. In illustrative embodiments, the test image is a grey-scale image having varying degrees of grey, from white to black. Knowing how the object 10 should look, the technician reviews the contrasting grey scale/shades at the appropriate boundary regions of the test image. Again, as noted above, the pressurized gas should be noticeably darker, in grey scale, than the generally clear or light images of the low attenuation portion of the object 10.

A number of factors contribute to determining whether the contrast is sufficient enough. Among other things, the size of the pixels, as well as their pitch, may impact the necessary contrast level. For example, a monitor with many pixels that are all very small and closely spaced together may have better contrast than monitors having larger pixels that are spaced farther apart. In addition, the display device magnification level of the image also can impact the contrast. Furthermore, the bit length of a monitor or detector can lead to improved or reduced contrast. Ultimately, the technician typically should be looking for relatively clearly defined boundaries between the gas and the lower attenuation portions of the object 10. The amount of contrast can be qualitatively and/or quantitatively defined. After the appropriate contrast is determined, many like objects may be imaged without repeating these same calibration steps.

Accordingly, if there is not enough contrast, the process moves to step 712, which increases the pressure within the chamber 43. This should further increase the density of the gas. The amount of the increase may be qualitatively or quantitatively defined. For example, the technician may be directed to increase the pressure by no more than a fixed amount for each iteration. Alternatively, the technician may increase the pressure an amount that is commensurate to the perceived lack of contrast. Either case (i.e., a fixed increase or other type of increase), however, may be considered to be an increase in the pressure as a function of the lack of sufficient contrast. In other words, this adjustment of pressure within the sealed chamber 43 is considered to be made has a function of the density of the low attenuation portion of the object 10.

There may be instances, however, where the contrast is inappropriate because the gas is too dense. This may be considered to be a "saturated" state. Accordingly, the technician may reduce the pressure in a conventional manner to bring the contrast back to a more appropriate state. Among other ways, the technician may simply open the valve mechanism 50 to relieve some of the pressure.

After increasing or decreasing the pressure within the chamber 43, the process loops back to step 706, which takes another test image and again determines if the contrast is appropriate. If the contrast is appropriate, then the process continues to step 716, which captures a plurality of different two-dimensional images of the object 10. For example, as discussed above, the CT machine 18 may take between 1000 and 2000 different two-dimensional images of the object 10 from all sides (i.e., about the entire 360 degree periphery of the object 10). Accordingly, to produce a plurality of different two dimensional images, the CT machine 18 rotates the object 10, relative to the x-ray source 22, which directs penetrating x-rays in a cone-like pattern toward and through the fixture 38 and object 10. Using the system 16 of FIG. 2, illustrative embodiments rotate the rotary table 28 while generating the two-dimensional images, thus rotating the object 10 about its longitudinal axis.

Conventional processes, such as program code executing on the computer, then may produce a three-dimensional image from the plurality of two-dimensional images (step 718). Although they may not necessarily be displayed on the display device 32 as the exact same size of the object 10, the three-dimensional images should be substantially representative of the actual topology and dimensions of the object 10. Accordingly, conventional measurement technology software may measure the three dimensional image to ascertain specific features and qualities of the object 10 itself.

The pressurized gas thus may be considered to form a "mold," "negative," or "shadow" of at least the outside surface of the object 10 being measured. The low attenuating portions may be reconstructed using its boundary with the gas. Of course, the high attenuation portions are readily visible on the image with or without the gas. Rather than show the low attenuating portions as clear or white, computer program code or other processes may color the low attenuation portions bounded by the gas. Such processes may be manual (e.g., performed by a technician) or automatic. This should highlight the low attenuation portions more clearly, enabling a user to better see and view the topological details.

Some embodiments automate various steps of the process using computer logic. For example, program code executing on the computer 34 may calculate whether, at step 708, there is an appropriate contrast between the low attenuation portion of the object 10 and the pressurized gas. The computer thus may have certain prescribed numerical thresholds to compare against to determine the desired contrast. In that case, the system 16 may repeatedly change the pressure until the contrasting shades, at the appropriate locations, are at least equal to or greater than a prescribed numerical value representing the difference between the shades. As another example, the gas may be added, and/or the pressure may be adjusted, using some automated means.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as preprogrammed hardware elements (e.g., application specific integrated circuits, FPGAs, and digital signal processors), or other related components.

In an alternative embodiment, the disclosed apparatus and methods (e.g., see the various flow charts described above) may be implemented at least in part as a computer program product for use with a computer system. Such implementation may include a series of computer instructions fixed either on a tangible medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or other remove device over the network (e.g., the Internet or World Wide Web). Of course, some embodiments of the invention may be implemented as a combination of both software (e.g., a computer program product) and hardware. Still other embodiments of the invention are implemented as entirely hardware, or entirely software.

Although the above discussion discloses various exemplary embodiments of the invention, it should be apparent that those skilled in the art can make various modifications that will achieve some of the advantages of the invention without departing from the true scope of the invention.

What is claimed is:

1. A method of imaging a heterogeneous object, the method comprising:

positioning the heterogeneous object within a fixture having a chamber, the heterogeneous object comprising a first non-gaseous portion and a second non-gaseous portion, the first non-gaseous portion having the property of attenuating x-rays more than the second non-gaseous portion, the second non-gaseous portion being substantially invisible to X-rays;

adding an inert gas to the chamber, the inert gas comprising at least one of argon, xenon, and krypton;

sealing the chamber to substantially contain the gas within the chamber;

increasing, after adding the inert gas, the pressure within the sealed chamber as a function of the density of the second non-gaseous portion of the object, the density of the gas increasing with the increased pressure within the sealed chamber;

penetrating x-rays through the object to produce a plurality of images of the object, the pressurized gas contrasting with the first non-gaseous portion and the second non-gaseous portion of the object in at least some of the plurality of images;

generating a three-dimensional representation of the object using the contrast produced by the pressurized gas in the plurality of images, the three-dimensional representation of the object showing topological details of the object; and measuring at least one of the topological object details using the three-dimensional representation of the object.

2. The method as defined by claim 1 wherein the gas comprises a mixture of gasses.

3. The method as defined by claim 1 wherein the gas includes xenon.

4. The method as defined by claim 1 wherein the pressure is greater than about 1 atmosphere and less than about 50 atmospheres.

5. The method as defined by claim 1 wherein the gas will not cause an oxidation reaction with the object.

6. The method as defined by claim 1 further comprising rotating the chamber to produce the plurality of images.

7. The method as defined by claim 1 wherein directing the x-rays comprises using a CT machine to generate the x-rays.

8. The method as defined by claim 1 wherein changing the pressure within the sealed chamber comprises:

generating at least one test image of the object at a first pressure; and changing the pressure within the chamber as a function of the contrast between the second non-gaseous portion and the gas as shown in the test image.

9. A method of imaging a heterogeneous object, the method comprising:

providing a the heterogeneous object comprising a first non-gaseous portion and a second non-gaseous portion, the first non-gaseous portion having the property of attenuating x-rays more than the second non-gaseous portion, the second non-gaseous portion being substantially invisible to X-rays;

positioning the heterogeneous object within a fixture having a chamber, the fixture having a valve for receiving a gas and normally sealing the chamber, the object being within the chamber;

positioning the fixture within an active region of a CT machine;

injecting inert gas into the chamber through a gas line fluidly connected to the valve, and the valve, the inert gas comprising at least one of argon, xenon, and krypton;

increasing, after injecting the inert gas, the pressure within the sealed chamber to increase the density of the gas within the chamber;

directing x-ray energy toward the active region of the CT machine to produce a plurality of two-dimensional images of the first non-gaseous portion of the object, the second non-gaseous portion of the object, and the pressurized gas; and generating a three-dimensional representation of the object from the plurality of images, the three-dimensional representation of the object comprising the first non-gaseous portion of the object and the second non-gaseous portion of the object, and distinguishing the first non-gaseous portion of the object and the second non-gaseous portion of the object from the gas, the three-dimensional representation of the object showing topological details of the object; and measuring at least one of the topological object details using the three-dimensional representation of the object.

10. The method as defined by claim 9 further comprising removing the gas line from fluid connection with the valve after injecting the gas into the chamber.

11. The method as defined by claim 10 wherein the fixture has a longitudinal rotational axis, directing x-ray energy comprising rotating the fixture about the rotational axis, wherein the gas line is removed before rotating the fixture.

12. The method as defined by claim 9 further comprising:
generating at least one test image of the object at a first pressure, the test image including a visual representation of the object and the gas, the gas and object respectively having contrasting shades in the visual representation; and changing the pressure within the chamber as a function of the contrasting shades in the test image.

13. The method as defined by claim 12 wherein the pressure is repeatedly changed until the contrasting shades are at least equal to or greater than a prescribed numerical value representing the difference between the shades.

14. The method as defined by claim 9 wherein the inert gas comprises a mixture of gasses.

15. The method as defined by claim 9 wherein the pressure is greater than about 1 atmosphere and less than about 50 atmospheres.

16. The method as defined by claim 9 wherein the plurality of images at least one of the plurality of images show two-dimensional representation of the object.

17. The method as defined by claim 9 wherein the three-dimensional representation of the object shows topological object details, the method further comprising measuring at least one of the topological object details.

18. The method as defined by claim 1 wherein increasing, after adding the inert gas, comprises:
viewing a test image after increasing the pressure at least once,
increasing the pressure within the sealed chamber a second time after viewing the text image.

* * * * *

UNITED STATES PATENT AND TRADEMARK OFFICE
CERTIFICATE OF CORRECTION

| | | |
|---|---|---|
| PATENT NO. | : 9,170,215 B2 | Page 1 of 1 |
| APPLICATION NO. | : 13/660235 | |
| DATED | : October 27, 2015 | |
| INVENTOR(S) | : O'Hare et al. | |

It is certified that error appears in the above-identified patent and that said Letters Patent is hereby corrected as shown below:

In col. 11, line 22 remove "and"

Signed and Sealed this
Fifteenth Day of March, 2016

Michelle K. Lee
*Director of the United States Patent and Trademark Office*